(12) United States Patent
Murray et al.

(10) Patent No.: US 10,959,827 B2
(45) Date of Patent: Mar. 30, 2021

(54) LIGAMENT FIXING AND A METHOD OF ATTACHING A LIGAMENT

(71) Applicants: ZIMMER GMBH, Winterthur (CH); David Wycliff Murray, Oxford (GB); John Joseph O'Connor, Oxford (GB)

(72) Inventors: David Wycliffe Murray, Oxford (GB); Russell Lloyd, Swindon Wiltshire (GB); Mona Alinejad, London (GB); John Joseph O'Connor, Oxford (GB)

(73) Assignee: Zimmer GmbH, Winterthur (CH)

( * ) Notice: Subject to any disclaimer, the term of this patent is extended or adjusted under 35 U.S.C. 154(b) by 265 days.

(21) Appl. No.: 16/028,911

(22) Filed: Jul. 6, 2018

(65) Prior Publication Data

US 2018/0311031 A1    Nov. 1, 2018

Related U.S. Application Data

(62) Division of application No. 14/927,941, filed on Oct. 30, 2015, now abandoned.

(30) Foreign Application Priority Data

Oct. 31, 2014   (GB) ...................................... 1419469

(51) Int. Cl.
*A61B 17/58* (2006.01)
*A61B 17/60* (2006.01)
(Continued)

(52) U.S. Cl.
CPC .............. *A61F 2/08* (2013.01); *A61F 2/0811* (2013.01); *A61F 2/389* (2013.01); *A61F 2/3836* (2013.01); *A61F 2/3859* (2013.01);
*A61F 2/4657* (2013.01); *A61F 2/4684* (2013.01); *A61F 2002/087* (2013.01);
(Continued)

(58) Field of Classification Search
CPC combination set(s) only.
See application file for complete search history.

(56) References Cited

U.S. PATENT DOCUMENTS 4,726,121 A    2/1988  Ray et al.
4,779,349 A   10/1988  Odensten et al.
(Continued)

FOREIGN PATENT DOCUMENTS

WO    WO-2011150238 A1    12/2011

OTHER PUBLICATIONS

U.S. Appl. No. 14/927,941, filed Oct. 30, 2015, Ligament Fixing and a Method of Attaching a Ligament.
(Continued)

*Primary Examiner* — Sameh R Boles
(74) *Attorney, Agent, or Firm* — Schwegman Lundberg & Woessner, P.A.

(57) ABSTRACT

An artificial ligament is provided having an elongate body and two ends, with a loop being provided at least one of the ends and a loop liner being provided within the loop. A kit of artificial ligaments is also provided with each ligament in the kit having a different fixed length. Also provided are methods for determining a length of artificial ligament to be used within a prosthetic knee joint, selecting a ligament from a range or kit of ligaments, and implanting a prosthetic knee joint assembly comprising an artificial ligament.

10 Claims, 6 Drawing Sheets

(51) Int. Cl.
  *A61F 2/00* (2006.01)
  *A61F 2/08* (2006.01)
  *A61F 2/38* (2006.01)
  *A61F 2/46* (2006.01)
  *A61F 2/30* (2006.01)

(52) U.S. Cl.
  CPC ............... *A61F 2002/0852* (2013.01); *A61F 2002/0888* (2013.01); *A61F 2002/30462* (2013.01); *A61F 2002/30537* (2013.01); *A61F 2002/30566* (2013.01); *A61F 2002/4658* (2013.01); *A61F 2210/0057* (2013.01)

(56) References Cited

U.S. PATENT DOCUMENTS

| | | |
|---|---|---|
| 4,883,486 A | 11/1989 | Kapadia et al. |
| 5,013,318 A | 5/1991 | Spranza, III |
| 5,026,389 A | 6/1991 | Thieler |
| 5,026,398 A | 6/1991 | May et al. |
| 5,108,433 A | 4/1992 | May et al. |
| 5,151,104 A | 9/1992 | Kenna |
| 5,688,276 A | 11/1997 | Shaffer |
| 2001/0049483 A1* | 12/2001 | Reay-Young .......... A61B 17/88 600/587 |
| 2006/0052795 A1* | 3/2006 | White .................... A61B 90/06 606/102 |
| 2016/0120639 A1 | 5/2016 | Murray et al. |

OTHER PUBLICATIONS

"U.S. Appl. No. 14/927,941, Examiner Interview Summary dated Mar. 29, 2017", 12 pgs.

"U.S. Appl. No. 14/927,941, Final Office Action dated Nov. 30, 2017", 8 pgs.

"U.S. Appl. No. 14/927,941, Non Final Office Action dated Mar. 13, 2018", 9 pgs.

"U.S. Appl. No. 14/927,941, Non Final Office Action dated Jun. 30, 2017", 9 pgs.

"U.S. Appl. No. 14/927,941, Response filed Jan. 22, 2018 to Final Office Action dated Nov. 30, 2017", 10 pgs.

"U.S. Appl. No. 14/927,941, Response filed May 30, 2017 to Restriction Requirement dated Mar. 29, 2017", 9 pgs.

"U.S. Appl. No. 14/927,941, Response filed Oct. 2, 2017 to Non Final Office Action dated Jun. 30, 2017", 14 pgs.

"United Kingdom Application No. 1419469.0, Search Report dated Aug. 26, 2015", 2 pgs.

* cited by examiner

LIGAMENT FIXING AND A METHOD OF ATTACHING A LIGAMENT

CLAIM OF PRIORITY

This application is a divisional of U.S. patent application Ser. No. 14/927,941, filed on Oct. 30, 2015, which claims the benefit of priority under 35 U.S.C. to United Kingdom Application No. 1419469.0, filed on 31 Oct. 2014, the benefit of priority of each of which is claimed hereby, and each of which are incorporated by reference herein in its entirety.

TECHNICAL FIELD

This invention relates to artificial knee ligaments and methods for implanting an artificially knee ligament, and is particularly, although not exclusively, concerned with artificial ligaments having looped ends.

BACKGROUND

The statements in this section merely provide a background to the present disclosure and may not constitute prior art.

Prosthetic knee joints replace one or more of the articulate surfaces of a patient's knee joint, and are employed to improve the strength and/or mobility of the joint or reduce pain of the patient. Sections of the bones being replaced may be diseased, injured, deteriorated or some combination of the three.

In many cases the surgeon performing knee replacement surgery will take steps to preserve the ligaments of the knee which connect the bones of the knee across the joint. In some cases the ligaments themselves may be diseased or damaged, or the resection necessary to remove diseased portions of the bones may disrupt the integrity of the ligaments. If the ligaments are removed as part of the surgery and cannot be reattached, a prosthetic knee joint is required which places greater constraints on the movement of the knee joint. This can be achieved through the use of an artificial knee ligament joining the two sides of the joint.

In one proposed artificial knee joint, artificial ligaments are attached to the prosthetic components by looping or tying the ends of the ligament over bosses or bollards provided on the prosthetic components. As the knee joint moves, the ligament is able to articulate around the body of the bollard as required. Whilst this articulation of the ligament prevents the ligament from being bent or kinked, over time the loops of the ligament can become worn.

Artificial knee ligaments are not required to be tensioned when installed, however it is undesirable for ligaments to be excessively long or loose as this could reduce the stability of the joint. For similar reasons, it is not desirable for an artificial ligament to be flexible. In one possible surgical procedure, both prosthetic components are first implanted before alternative length ligaments are offered up by the surgeon and one can be selected which the surgeon judges will have suitably laxity when fitted. In order to fit the ligament, the knee must be overflexed to provide the necessary access to the ligament fixings on each side of the joint. This also has the effect of separating the bones of the knee and hence excess force is required to attach the ligament. A device may be required to pull or lever the ligament onto a fixing and there is a significant risk of damaging the artificial ligament in the process.

In order to avoid this excessive manipulation of the knee joint and potential damage to the ligament, artificial ligaments have been designed with loops which are formed at the operative site, allowing the length of a ligament to be adjusted subsequently to its attachment to both sides of the joint.

WO 2011/1502538 discloses a prosthetic knee joint assembly with an artificial ligament link. The ligament link extends between first and second ends and includes an outer wall defining an interior longitudinal passage portion. First and second apertures extend through the wall. The first end extends through the first and second apertures and the longitudinal passage portion to define a first adjustable loop, and the second end extends through the first and second apertures and the longitudinal passage portion to define a second adjustable loop.

It is speculated that ligaments with preformed loops are still more reliable with less chance of becoming loose or failing after implantation. Hence, using a ligament with fixed loops is desirable in some cases.

The present disclosure relates to a method for implanting an artificial ligament of fixed length without requiring the knee joint to be overflexed, or excessive force being applied to the ligament. An artificial ligament particularly suited for this use is also provided.

STATEMENTS OF INVENTION

According to an aspect of the present invention there is provided an artificial knee ligament substantially formed of a first material, comprising an elongate body of fixed length and two ends, wherein a loop is provided at each of the ends and a portion of a second material is provided on at least one loop.

According to another aspect of the present invention there is provided an artificial knee ligament comprising an elongate body and two ends, wherein a loop is provided at at least one of the ends; and a loop liner provided within the loop.

The length of the ligament and/or the size of the loop may be fixed. The ligament may be configured to couple to a fixing provided on either a femoral or tibial component of a prosthetic knee joint.

The loop liner may be provided in the area of the loop which contacts the fixing of the prosthetic component. In this way, the loop liner may be provided covering an inside face of the loop. The loop liner may be formed from a different material to the body of the ligament. The loop liner may be formed from polyethylene. The loop liner may be shaped to sit between the fixing of the prosthetic knee component, and the ligament loop. The loop liner may be moulded onto the loop of the ligament or alternatively, the loop liner may comprise a thimble which is trapped within the eye of the loop. Other forms of loop liner may also be possible.

The loop liner may be resilient and may be elastically deformable to allow the ligament loop to be pushed over an enlarged head of the fixing of the prosthetic component.

According to another aspect of the present invention there is provided a method of implanting a prosthetic joint assembly, comprising a first component for attaching to a first bone (of the joint), a second component for attachment to a second bone (of the joint) and an artificial ligament, comprising the steps of: implanting the first prosthetic component into a patient;
coupling the preformed artificial ligament to the prosthetic components; and implanting the second prosthetic component into the patient.

According to another aspect of the present invention there is provided a method of implanting a prosthetic knee joint assembly, comprising a tibial component, a femoral component and an artificial knee ligament, comprising the steps of:

implanting the tibial component or the femoral component into a patient;

coupling a preformed artificial ligament to the prosthetic components; implanting the other component into the patient.

The tibial component may be implanted before the femoral component or alternatively, the femoral component may be implanted before the tibial component. The first prosthetic component may be implanted in a temporary manner.

The method may further comprise the step of determining an appropriate length for a replacement knee ligament to link the tibial and femoral components of the prosthetic knee joint. This step may be completed prior to the step of coupling the preformed artificial ligament to the prosthetic components.

Additionally or alternatively, the method may further comprise the step of selecting a preformed artificial ligament of a suitable length from a set of artificial ligaments. This step may be completed prior to the step of coupling the preformed artificial ligament to the prosthetic components.

The step of installing a final meniscal bearing may be performed prior to the step of implanting the second prosthetic component into the patient. Alternatively the step of installing a temporary meniscal spacer may be performed instead and a final meniscal component may be installed between the tibial and femoral components of the prosthetic knee joint in an additional step which may be performed subsequently to the step of implanting the second prosthetic component into the patient.

The tibial prosthetic component may comprise a fixed knee bearing.

The method may be performed using the artificial ligament provided by a previously mentioned aspect of the invention.

According to another aspect of the present invention there is provided a method of determining a suitable length for an artificial ligament for use in a prosthetic joint assembly comprising a first prosthetic component for attaching to a first bone and a second prosthetic component connected to a second bone. The method comprising the steps of:

coupling a trial first component to the first bone of a patient in a temporary manner;

creating a trial ligament using an elongate element extended around a fixing on the trial first component and a second fixing on a previously implanted second component to form a continuous band;

cutting the band and removing the trial ligament from the surgical site; and measuring the reassembled band.

According to another aspect of the present invention there is provided a method of determining a suitable length for an artificial knee ligament comprising the steps of:

coupling first and second prosthetic components to a patient in a temporary manner;

creating a trial ligament using an elongate element extended around a first fixing on the first prosthetic component and a second fixing on the second component to form a continuous band;

cutting the band and removing the trial ligament from the surgical site; and measuring the length of the reassembled band.

The first and/or second prosthetic components may be trial prosthetic components. Alternatively or additionally, either or both of the prosthetic components may be the final prosthetic components. The fixings provided on the femoral and tibial components may be bollards.

The method may further comprise the step of installing a trial meniscal component between the tibial and femoral components of the prosthetic knee joint. This step may be performed prior to the step of creating a trial ligament. The trial meniscal component may also be the final meniscal component.

The elongate element used in the method may comprise a trial ligament with one looped end and one open end which can be tied. Alternatively the elongate element may be a zip tie or any other elongate element suitable for being selectively formed into a continuous band.

A pin may be used to mark the required length of elongate element whilst fitted to the patient. Alternatively or additionally, the elongate element may comprise markings allowing the length of the band to be determined from the markings on the elongate element.

The method according to this aspect of the present invention may be used to determine an appropriate length for a replacement knee ligament to link the tibial and femoral components as described in any preceding aspect of the invention.

According to another aspect of the present invention there is provided an artificial knee joint assembly comprising a tibial component, a femoral component and an artificial knee ligament which may be the artificial ligament as described in any preceding aspect of the invention.

According to another aspect of the present invention there is provided a kit of artificial knee ligaments wherein each ligament within the kit has a different fixed length. The ligaments in the kit may be as described in any preceding aspect of the invention.

According to another aspect of the present invention there is provided instrumentation for measuring between first and second ligament fixings of prosthetic components comprising: an elongate body, an arcuate portion provided at or towards one end of the elongate body and a slideable jaw, configured to slide along the elongate body. The arcuate portion may be configured to closely engage the first fixing. The slideable jaw may be configured to engage the second fixing.

The position of the slideable jaw may be selectively fixable relative to the elongate body. The jaw and the elongate body may be provided with cooperating formations and the jaw may fixed by rotating a portion of the jaw to engage the cooperating formations.

The elongate body may further comprise a measurement scale. The measurement scale may indicate the size of artificial ligament required to link the first and second fixings.

According to another aspect of the present invention, there is provided instrumentation for measuring between fixings of prosthetic components comprising: an elongate body with first and second ends; wherein the first end is configured to couple with a first fixing on a first prosthetic component; and the second end comprises a measurement scale. The scale allows the distance from the first fixing to a second fixing on a second prosthetic component to be measured. The scale may indicate the size of artificial ligament required to link the first and second fixings.

The instrumentation may further comprise a jaw which may be axially slideable along the measurement scale of the elongate body. The jaw may be selectively lockable relative to the elongate body. The jaw and the elongate body may be provided with cooperating features and the jaw may be locked by rotating a portion of the jaw to engage the cooperating features. Alternatively or additionally, the jaw may be configured to engage a second fixing on a second prosthetic component.

BRIEF DESCRIPTION OF THE DRAWINGS

For a better understanding of the present invention, and to show more clearly how it may be carried into effect, reference will now be made by way of example, to the accompanying drawings, in which.

DETAILED DESCRIPTION

Figure 1:
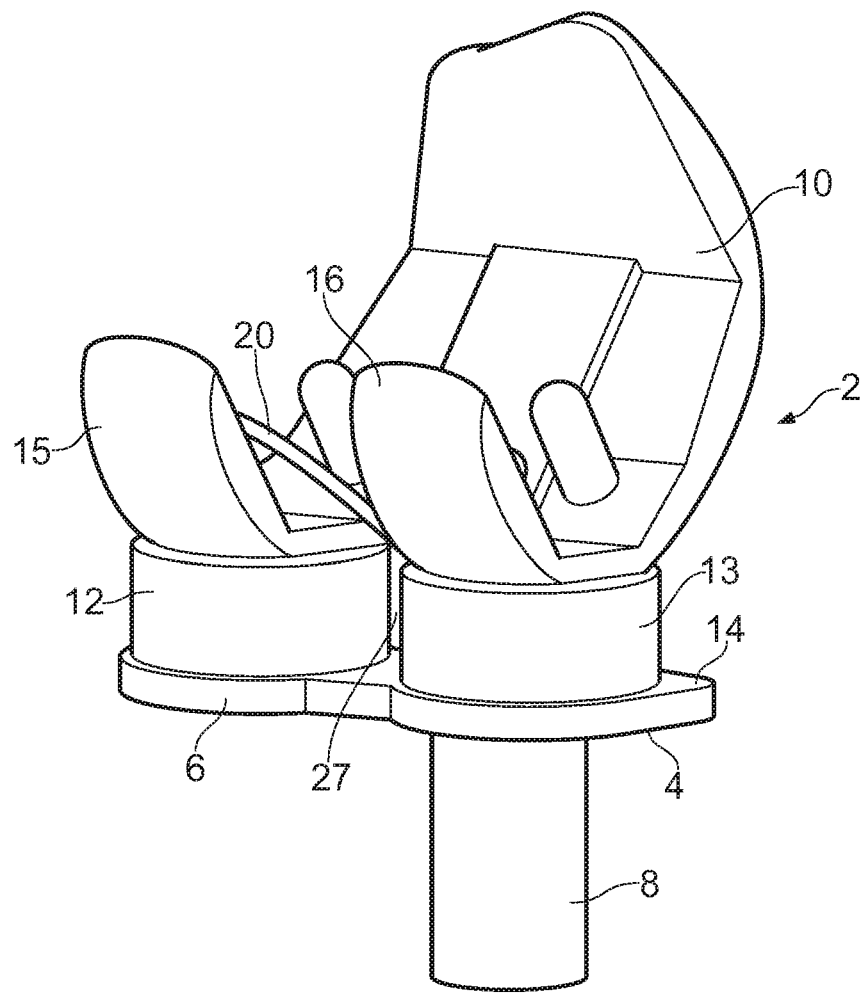
FIG. 1 shows a full knee replacement prosthetic knee joint comprising an artificial ligament according to an example of the present invention.

Referring to FIG. 1, a knee prosthesis 2 comprises a tibial component 4 having a tibial tray 6 integrally formed with a stem 8, a femoral component 10 and a pair of bearing components 12, 13. The bearing components 12, 13 separate the tibial component 4 and the femoral component 10 and are formed with proximal and distal bearing surfaces which engage corresponding bearing surfaces 14, 15, 16 on the tibial tray 6 and on the femoral component 10. These various bearing surfaces enable the tibial component 4 to rotate and translate relative to the femoral component 10. The bearing components 12, 13 may be meniscal bearing components, rotational platform bearing components, or may be fixed bearing components. The combination of the bearing surfaces 14, 15, 16 and the bearing components 12, 13 allows the knee prosthesis to achieve a similar range of movements to an anatomical knee joint.

An artificial knee ligament 20 is provided within the knee prosthesis 2 to restrict undesirable movements of the knee prosthesis, improving the stability of the joint in use, as well as reducing the risk of dislocation of the bearing components 12, 13. The ligament 20 is elongate in form and constructed substantially of a first biocompatible material which has high tensile strength and stiffness.

Figure 2:
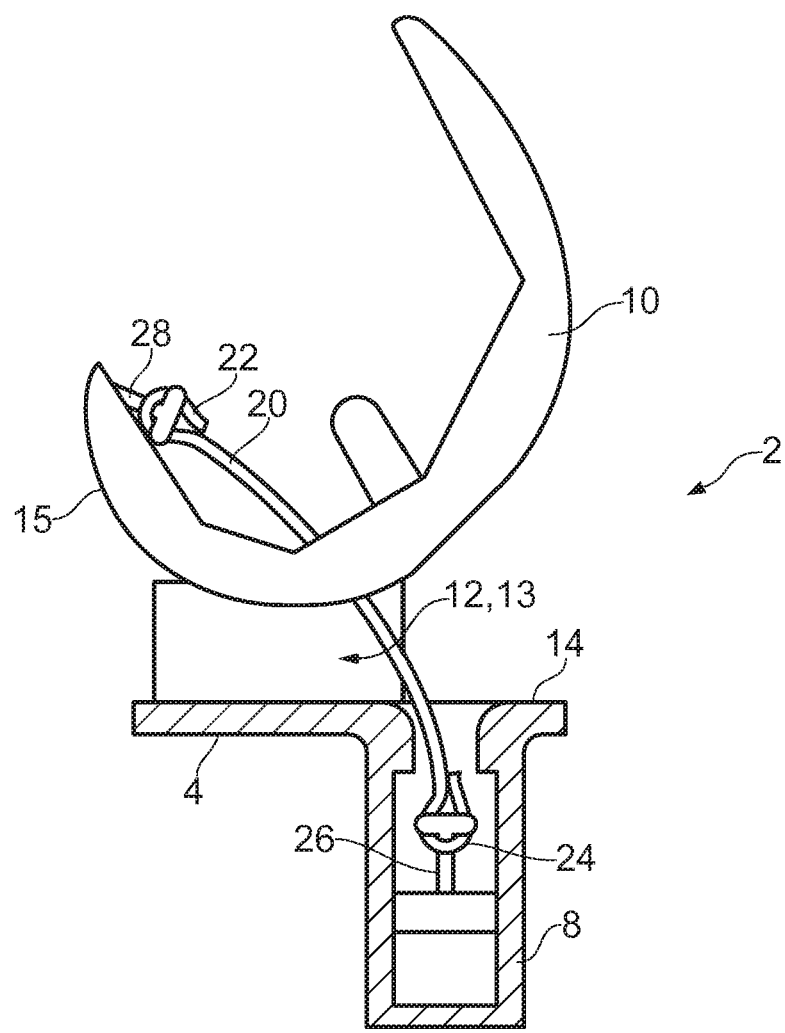
FIG. 2 is a sectional view of a full knee replacement prosthetic knee joint comprising an artificial ligament according to an example of the present invention.

With reference to FIG. 2, the ligament 20 is terminated at the proximal end by a proximal loop 22 and at the distal end by a distal loop 24, both loops having a fixed size. In the embodiment shown, the loops are formed by looping back the material at each end of the ligament to form the loops, and gluing the free ends of the ligament back to itself to secure the loop. Alternatively, another method for securing the loop could be used, for example the individual fibres of the ligament could be separated, then woven back in to the ligament to secure the loop or the ligament could be passed through a washer looped on one side of the washer then the individual fibres of the ligament could be fed back though holes in the washer to secure the loop.

The distal loop 24 is connected to a fixing provided on the tibial component 4 which may comprise a tibial bollard 26 and the proximal loop 22 is connected to a fixing provided on the femoral component 10 which may comprise a femoral bollard 28. The bollards 26, 28 comprise a neck portion and a head portion, with the neck portion being narrower in form than the head portion. When the ligament 20 is fitted to the knee prosthesis 2, the loops 22, 24 rest on the neck portions of the bollards and are prevented from sliding or working themselves off the bollard by the wider head portion.

Figure 3:
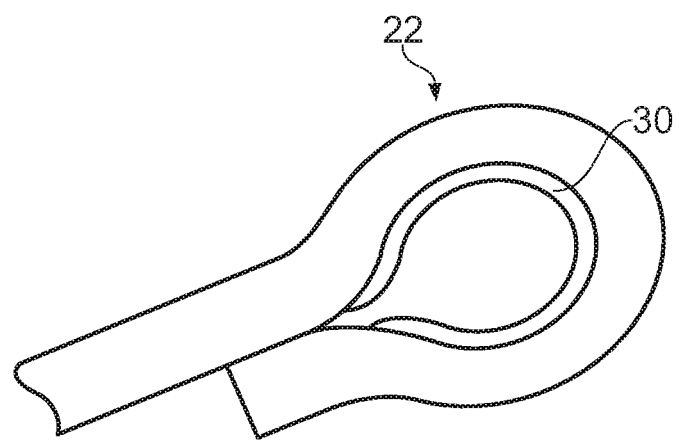
FIG. 3 shows an artificial knee ligament according to one example of the present invention.

With reference to FIG. 3, a wear portion 30, is provided on the inside of the proximal and distal loops 22, 24. In the embodiment shown in FIG. 3, the wear portion 30 is moulded into the loop to form a single component. The wear portion 30 is located in the area of each loop 22, 24 where the loop contacts the neck of the tibial or femoral bollard when the ligament is fitted. The wear portion may be shaped or dipped to rest against the fixing in use. The wear portion 30 may be formed in a second biocompatible material, such as polyethylene, which has a greater resistance to abrasive wear than the first biocompatible material which forms the ligament. The wear portion 30 may comprise a resilient ring of material and may be configured to pull the loop towards a closed or partially closed configuration. The wear portion 30 may thus be configured to grip the bollard 26, 28 when fitted, further reducing the possibility of the ligament becoming disconnected. The wear portion 30 may be elastically deformable allowing the loops 22, 24 to become substantially circular in an open configuration. In the open configuration, as shown in FIG. 3, the loops can be fitted over the head portion of the bollards 26, 28.

Figure 4:
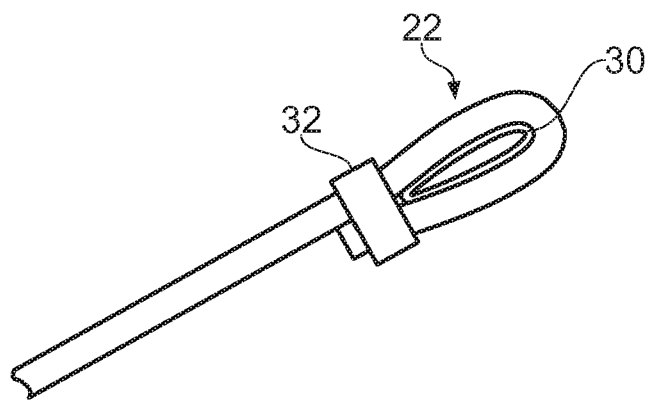
FIG. 4 shows an artificial knee ligament according to a second example of the present invention.

With reference to FIG. 4, the loops 22, 24 of the artificial ligament 20 may be further secured by the use of ferrules 32. In the embodiment shown in FIG. 4 the wear portions 30 comprise thimbles which are formed as separate loops which are trapped within the eyes of the ligament loops 22, 24. The thimbles are resilient and may be configured hold the loops in the closed condition when not fitted to the bollards, as shown in FIG. 4.

Figure 5:
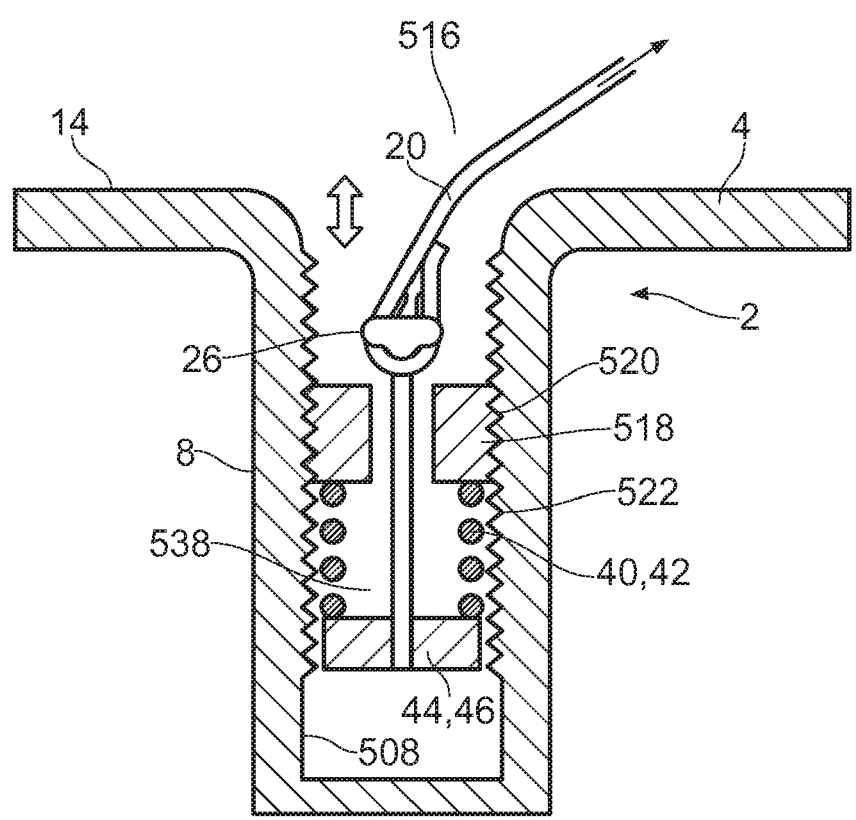
FIG. 5 is a sectional view showing an example implementation of a biasing element and tension element used to provide the desired stiffness to an artificial ligament according to the present invention.

With reference to FIG. 5, a biasing element 538 may be provided between the tibial bollard 26 and the tibial component 4. The biasing element 538 is provided within a bore 508 of the stem 8 of the tibial component 4. The tibial bollard 26 may also be received within the bore 508. The bore 508 opens onto the bearing surface 14 of the tibial tray 6. The artificial ligament 20 extends into the bore 508 through a space 516 between the bearing components 12, 13, so that the artificial ligament 20 substantially does not interfere with the bearing components 12, 13 during normal articulation of the prosthesis.

The biasing element 538 comprises a resilient element 40. In the illustrated embodiment, the resilient element 40 is a coiled compression spring 42 and the bearing element 44 is a plate 46. However, the resilient element 40 may consist of or comprise any appropriate spring or springs, for example a Belleville washer or an elastomeric member. An appropriate bearing element may be selected according to the choice of resilient element or may be omitted if not required.

With continued reference to FIG. 5, the knee prosthesis also comprises a tensioning element 518. The tensioning element 518 is mounted in the stem 8 of the tibial component 4. The tensioning element 518 is cylindrical and formed with an external thread 520 which engages with an internal thread 522 formed in the bore 508. The tensioning element 518 acts between the biasing element 538 and the tibial component 4. The tensioning element 518 is adjustable, to allow the tension in the ligament 20 to be set to appropriately.

In the embodiment shown, the resilient element 538 and the tensioning element 518 are both provided on the tibial component 4 of the knee prosthesis 2. It is equally envisaged that both could be provided on the femoral component 10, or one could be provided on each of the prosthetic components 12, 13. Alternatively one or both could be omitted.

Figure 6:
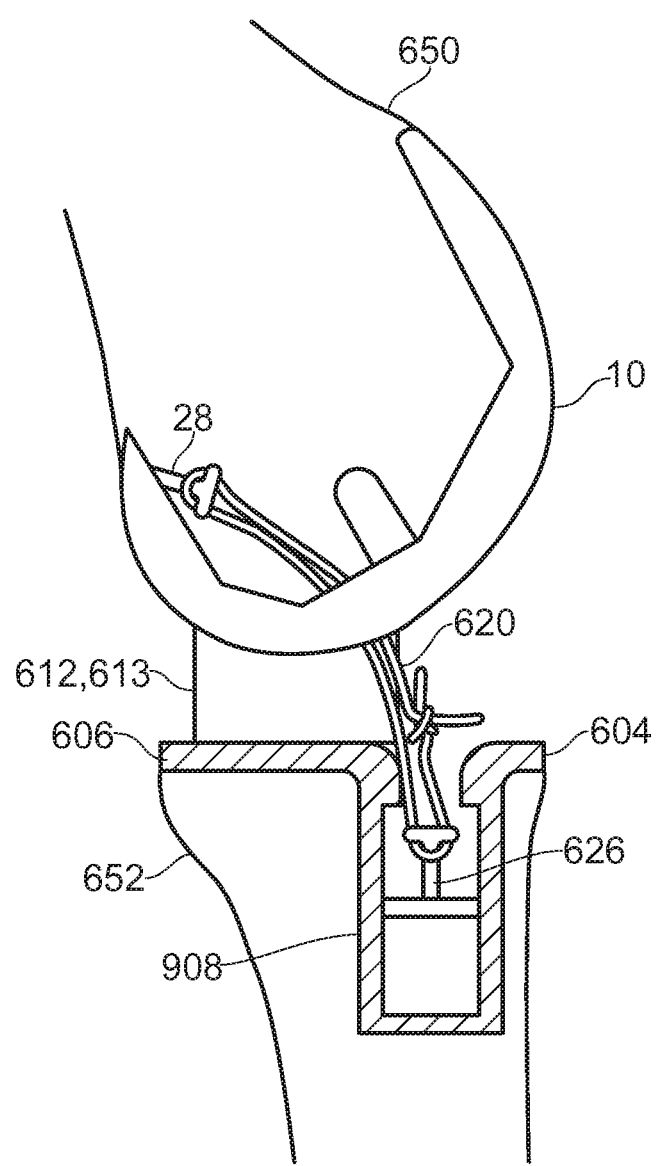
FIG. 6 shows an implanted trial prosthetic knee joint assembly according to an example of the present invention, including a trial tibial component and a trial artificial ligament.

With reference to FIG. 6, in order to determine a suitable length of artificial ligament 20 to be fitted to the knee prosthesis 2, a trial ligament 620 may be created. When the trial ligament is created, the tibial component 4 of the knee prosthesis 2 may not have been implanted and hence a trial tibial component 604 may be used temporarily within the knee joint assembly. The trial tibial component 604 also comprises a tibial tray 606, a stem 608 and a tibial bollard 626. The connection between the trial tibial component 604 and the trial ligament 620 is substantially the same as the connection between the tibial component 4 and the ligament 20 as shown in FIG. 1. Similarly, the final bearing components 12, 13 may not be fitted, and trial bearing components 612, 613 may be temporarily used in the assembly when creating the trial ligament 620. The trial ligament 620 can be formed by tying a length of surgical string around the femoral bollard 28 and the trial tibial bollard 626. Alternatively the trial ligament could be formed from a zip tie or any other suitable elongate element which is selectively connectable to form a continuous band. In some cases, the trial tibial component 604 may be the final tibial component 4 which has been fitted in a temporary manner.

In order to address the shortcomings recognised in a method for implanting a prosthetic knee joint, as presented in the background section above, improved methods of implanting the prosthesis 2 are herein described.

In one method of implanting the prosthesis 2, the femoral component 10 is implanted into the distal end of a femur 650; the trial tibial component 604 is fitted temporarily to the proximal end of a tibia 652 such that the tibial tray 606 rests of the resected proximal end of the tibia 652. Trial bearing components 612, 613 are placed between the femoral component 10 and the trial tibial component 604. The trial ligament 620 is then created by tying off a length of surgical string after it has been tightened around the femoral bollard 28 and the trial tibial bollard 626. The trial ligament 620 is then cut away and removed from the operative site. The trial ligament 620 can then be reassembled into a closed loop and the length of the loop measured to determine the length of artificial ligament 20 required to be fitted into the knee prosthesis 2.

In an alternative method (not shown), the trial ligament 620 could comprises a tie which is colour coded, such that the length of ligament required can be determined by the colour of the trial ligament 620 at the position it has been tied. Alternatively, the trial ligament 620 could comprise a zip tie with a ratchet head and rather than being tied, the zip tie could be tightened around the bollards using the ratchet head, the colour of the tie at the position of the head could be noted and the tie could then be undone and removed from the operative site. Alternatively, rather than being colour coded, the tie could be marked with numbers or letters, denoting the length of tie used.

Once the length of trial ligament 620 has been determined, an artificial ligament 20 of a suitable length may be selected from a range or kit of artificial ligaments available.

Figure 7:
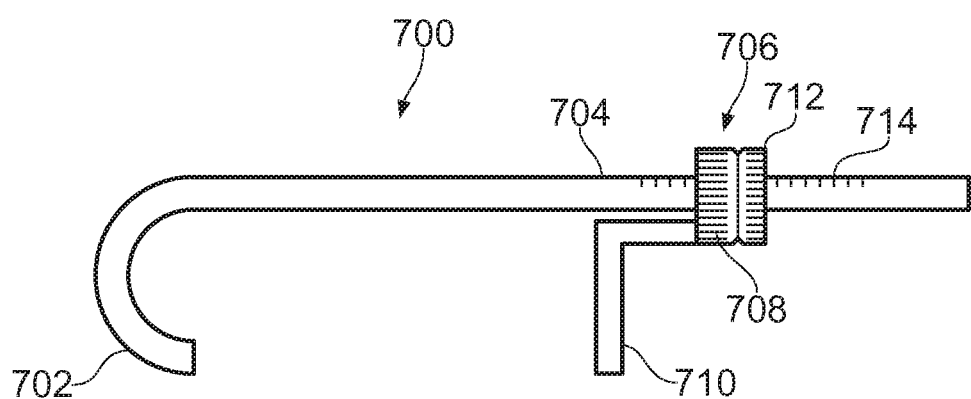
FIG. 7 shows instrumentation for measuring the required length of a ligament.

With reference to FIG. 7, a ligament gauge 700 can alternatively be used to determine the length of ligament required. The ligament gauge 700 comprises a hook 702, which is configured to couple with a femoral bollard 28, and an elongate shaft portion 704. A slider 706 is configured to be axially movable along the shaft 704. The slider comprises a body 708, a jaw 710 and a locking component 712. The locking component 712 can be rotated relative to the slider body 708 and shaft 704 to lock the slider axially with respect to the shaft 704. Measurement markings 714 are provided on the shaft for the required length of ligament to be read off. In use, the hook 702 is coupled to the femoral bollard 28 of a prosthetic component implanted on to the femur of a patient. The slider is moved along the shaft until the jaw 710 engages with the tibial bollard 26. The locking component is then rotated to lock the position of the slider. The locking action may be achieved through the use of tabs (not shown) provided on the inside of the locking component 712 which engage with grooves in the shaft 704. The shaft may be configured such that the tabs on the locking component 712 do not engage the shaft 704 in the unlocked position. The ligament gauge 700 can be rotated about the femoral bollard 28 to disengage the jaw 710 from the tibial bollard 26. The hook 702 can then be unhooked from the femoral bollard 28 and the gauge can be removed. In this way, the measurement recorded on the ligament gauge 700 can be read after the gauge has been removed from the operative site.

Once a suitable artificial ligament 20 has been selected, the trial tibial component 604 is removed from the joint. The distal loop 24 of the artificial ligament 20 is attached to the tibial bollard 26 of the final tibial component 4. The proximal loop 22 of the artificial ligament 20 is then attached to the femoral bollard 28 of the femoral component 10. By attaching the artificial ligament to both the tibial component 4 and the femoral component 10 before the tibial component 4 is finally implanted, the problem highlighted in the current methods is avoided.

At this stage the trial bearing components 612, 613 may be removed, and the final bearing components 12, 13 may be inserted between the tibial tray 6 and the bearing surfaces 15, 16 of the femoral component 10. Alternatively, if desirable, a meniscal spacer (not shown) which is slightly thinner than the final bearing components 12,13 can be fitted to the prosthetic joint 2 to reduce loading of the ligament 20 during the final stages of the implantation. The tibial component 4 is then implanted into the proximal end of the tibia 652.

If the meniscal spacer or the trial bearing components 612, 613 are still present within the joint, they are now removed and the final bearing components 12, 13 are fitted to the knee prosthesis 2.

Although in the example shown, the final femoral component 10 is implanted first, and the tibial component 4 of the knee prosthesis is then fitted loosely or a suitable trial tibial component 604 is fitted to allow the required length of the artificial ligament 20 to be determined, it is equally envisaged that the final tibial component 4 could be implanted first, and the femoral component 10 or a suitable trial femoral component (not shown) could be fitted thereafter to allow the required artificial ligament length to be determined. It is also considered, that both the femoral and tibial components could be trial components and could be fitted temporarily whilst the trial ligament 620 is formed.

What we claim is:
1. An instrument for measuring between first and second ligament fixings of prosthetic components comprising:
    an elongate shaft portion including a proximal end and a distal end and defining a longitudinal shaft axis;

an arcuate portion extending from the distal end of the elongate shaft portion;

a slideable jaw operably coupled to the elongate shaft portion, wherein the slideable jaw is configured to slide along the elongate shaft portion to adjust an axial distance between the arcuate portion and the slideable jaw; and a locking element operable to fix an axial position of the slideable jaw relative to the arcuate portion by rotation of the locking element about the longitudinal shaft axis.

2. The instrument of claim 1, wherein the elongate shaft portion further comprises a measurement scale.

3. The instrument of claim 2, wherein the measurement scale indicates the size of artificial ligament required to link the first and second ligament fixings.

4. The instrument of claim 1, wherein the arcuate portion is configured to closely engage the first ligament fixing.

5. The instrument of claim 1, wherein the slideable jaw is configured to engage the second ligament fixing.

6. The instrument of claim 1, wherein the arcuate portion comprises a hook that extends from the elongate shaft portion in a first direction, and the slideable jaw extends from the elongate shaft portion in a second direction.

7. The instrument of claim 6, wherein the first and second directions are the same.

8. The instrument of claim 1, wherein the arcuate portion is configured to engage the first ligament fixing and the slideable jaw is configured to engage the second ligament fixing.

9. The instrument of claim 8, further comprising a measurement scale disposed on the elongate shaft portion for determining a required length of a ligament.

10. The instrument of claim 9, wherein the first ligament fixing comprises a femoral bollard and the second ligament fixing comprises a tibial bollard.

* * * * *